United States Patent
Wegner

(10) Patent No.: US 6,632,495 B1
(45) Date of Patent: Oct. 14, 2003

(54) PYRIMIDINE-BASED CROSSLINKING AGENTS

(75) Inventor: Egon Wegner, Veitshöchheim (DE)

(73) Assignee: BASF Coatings AG, Munster (DE)

( * ) Notice: Subject to any disclaimer, the term of this patent is extended or adjusted under 35 U.S.C. 154(b) by 0 days.

(21) Appl. No.: 09/937,651

(22) PCT Filed: Mar. 30, 2000

(86) PCT No.: PCT/EP00/02785

§ 371 (c)(1),
(2), (4) Date: Nov. 7, 2001

(87) PCT Pub. No.: WO00/59894

PCT Pub. Date: Oct. 12, 2000

(30) Foreign Application Priority Data

Apr. 1, 1999 (DE) .......................... 199 14 898

(51) Int. Cl.[7] ..................... C07D 239/02; C07D 239/28
(52) U.S. Cl. ................. 428/35.8; 252/183.11; 427/428; 428/458; 428/460; 428/461; 428/463; 544/317
(58) Field of Search ............................. 523/108, 113, 523/548, 257, 258, 262; 526/262, 263, 242; 544/242, 336, 317; 548/335.1; 428/357, 361, 375, 411.1, 413, 417, 418, 35.8, 458, 460, 461, 463; 427/428; 252/183.11

(56) References Cited

U.S. PATENT DOCUMENTS

| | | | |
|---|---|---|---|
| 3,639,147 A | 2/1972 | Benefiel et al. ............. 117/73 |
| 3,883,532 A | 5/1975 | Begland ................ 260/256.4 |
| 3,953,644 A | 4/1976 | Camelon et al. ........... 428/220 |
| 4,144,128 A * | 3/1979 | Hildebrand et al. .......... 195/63 |
| 4,220,679 A | 9/1980 | Backhouse ................ 427/401 |
| 4,444,954 A | 4/1984 | Mels et al. ................ 525/124 |
| 4,489,135 A | 12/1984 | Drexler et al. ............ 428/423.1 |
| 4,558,090 A | 12/1985 | Drexler et al. ............ 524/591 |
| 4,576,868 A | 3/1986 | Poth et al. .............. 428/423.1 |
| 4,675,234 A | 6/1987 | Sachs et al. ............... 428/328 |
| 4,710,542 A | 12/1987 | Forgione et al. ............ 525/127 |
| 4,719,132 A | 1/1988 | Porter, Jr. ................ 427/409 |
| 4,730,020 A | 3/1988 | Wilfinger et al. ........... 524/555 |
| 4,851,460 A | 7/1989 | Stranghöner et al. ........ 523/407 |
| 4,880,867 A | 11/1989 | Gobel et al. ............... 524/507 |
| 4,939,213 A | 7/1990 | Jacobs, III et al. ......... 525/329.9 |
| 4,945,128 A | 7/1990 | Hille et al. ............... 524/591 |
| 4,981,759 A | 1/1991 | Nakatani et al. ............ 428/626 |
| 5,075,372 A | 12/1991 | Hille et al. ............... 524/839 |
| 5,084,541 A | 1/1992 | Jacobs, III et al. ......... 528/45 |
| 5,334,420 A | 8/1994 | Hartung et al. ............ 427/407.1 |
| 5,342,882 A | 8/1994 | Göbel et al. .............. 524/832 |
| 5,356,669 A | 10/1994 | Rehfuss et al. ............ 427/407 |
| 5,416,136 A | 5/1995 | Konzmann et al. ......... 523/414 |
| 5,418,264 A | 5/1995 | Obloh et al. .............. 523/414 |
| 5,425,970 A | 6/1995 | Lahrmann et al. .......... 427/493 |
| 5,439,950 A * | 8/1995 | Liao et al. ................ 523/108 |
| 5,474,811 A | 12/1995 | Rehfuss et al. ........... 427/407.1 |
| 5,486,384 A | 1/1996 | Bastian et al. ............. 427/493 |
| 5,512,322 A | 4/1996 | Hille et al. .............. 427/407.1 |
| 5,552,496 A | 9/1996 | Vogt-Birnbrich et al. .... 525/440 |
| 5,569,705 A | 10/1996 | Vogt-Birnbrich et al. .... 524/591 |
| 5,571,861 A | 11/1996 | Klein et al. ............... 524/591 |
| 5,601,880 A | 2/1997 | Schwarte et al. .......... 427/407.1 |
| 5,605,965 A | 2/1997 | Rehfuss et al. ............ 525/100 |
| 5,623,016 A | 4/1997 | Klein et al. ............... 524/591 |
| 5,654,391 A | 8/1997 | Göbel et al. .............. 528/71 |
| 5,658,617 A | 8/1997 | Göbel et al. ............. 427/372.2 |
| 5,686,531 A | 11/1997 | Engelke et al. ............ 525/111 |
| 5,691,419 A | 11/1997 | Engelke et al. ............ 525/208 |
| 5,691,425 A | 11/1997 | Klein et al. ............... 525/455 |
| 5,716,678 A | 2/1998 | Röckrath et al. ......... 427/407.1 |
| 5,760,128 A | 6/1998 | Baltus et al. .............. 524/591 |
| 6,001,915 A | 12/1999 | Schwarte et al. ........... 524/457 |

FOREIGN PATENT DOCUMENTS

| | | | | |
|---|---|---|---|---|
| DE | 19960433 A1 * | 7/2001 | ......... C07D/239/28 |
| EP | 0 038 127 A1 | 3/1981 | ............ B05D/7/26 |
| EP | 0 245 700 A2 | 4/1987 | ......... C07D/251/54 |
| EP | 0 249 201 A2 | 6/1987 | ............ C09D/3/58 |
| EP | 0 276 501 A2 | 9/1987 | ............ C11D/1/42 |
| EP | 0 320 552 A1 | 12/1987 | ............ B05D/7/26 |
| EP | 0 299 148 A2 | 4/1988 | ......... C08G/18/08 |
| EP | 0 354 261 A1 | 8/1988 | ......... C08G/18/50 |
| EP | 0 394 737 A1 | 4/1990 | ......... C09D/175/06 |
| EP | 0 401 565 A1 | 5/1990 | ............ C09D/5/02 |
| EP | 0 424 705 A2 | 10/1990 | ......... C08F/283/00 |
| EP | WO 91/13923 | 9/1991 | ......... C08G/18/08 |
| EP | WO92/17546 | 10/1992 | ......... C08L/75/04 |
| EP | WO 92/22615 | 12/1992 | ......... C09D/151/08 |
| EP | 0 590 484 A1 | 9/1993 | ......... C08G/18/08 |
| EP | 0 594 068 A1 | 10/1993 | ......... C09D/201/02 |
| EP | 0 594 071 A1 | 10/1993 | ......... C09D/201/02 |
| EP | 0 594 142 A1 | 10/1993 | ......... C08L/57/12 |
| EP | 0 624 577 A1 | 5/1994 | ......... C07D/251/70 |
| EP | WO94/10211 | 5/1994 | ............ C08F/8/30 |
| EP | WO94/10212 | 5/1994 | ............ C08F/8/30 |
| EP | WO94/10213 | 5/1994 | ............ C08F/8/30 |
| EP | WO 94/22968 | 10/1994 | ......... C09D/133/06 |
| EP | WO 94/22969 | 10/1994 | ......... C09D/133/06 |
| EP | WO 95/14721 | 6/1995 | ......... C08F/290/14 |
| EP | WO97/12945 | 4/1997 | ......... C09D/5/04 |
| EP | WO97/49745 | 12/1997 | ......... C08G/18/08 |
| EP | WO97/49747 | 12/1997 | ......... C08G/18/75 |
| GB | 862974 | 12/1956 | |
| GB | 20 12 191 A | 12/1978 | ......... C05D/1/36 |

* cited by examiner

*Primary Examiner*—Sandra M. Nolan

(57) ABSTRACT

Pyrimidine-based crosslinking agents for thermally curable compositions, especially thermally curing coating materials, adhesive, sealing compounds or compounds for producing moldings.

15 Claims, No Drawings

PYRIMIDINE-BASED CROSSLINKING AGENTS

The present invention relates to novel pyrimidine-based crosslinking agents for thermally curable compositions, especially thermally curable coating materials, adhesives, sealing compounds or compounds for producing moldings. Triazine-based crosslinking agents are known. They comprise tris(alkoxy-carbonylamino)triazines of the formula

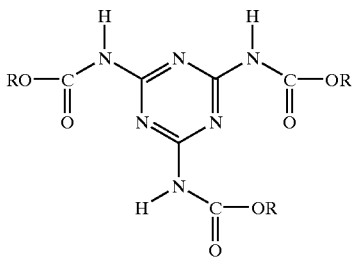

in which the radical R stands for alkyl, cycloalkyl or aryl radicals.

These tris(alkoxycarbonylamino)triazines, their preparation, and thermally curable compositions in which they are present as crosslinking agents are described in the patents U.S. Pat. No. 4,939,213, U.S. Pat. No. 5,084,541, U.S. Pat. No. 5,288,865 or EP-A-0 624 577. These crosslinking agents offer numerous advantages; however, owing to their highly symmetrical structure, they tend to crystallize from the thermally curable compositions, which is why only a few derivatives, such as the mixed methyl and butyl esters (R=methyl, butyl), for instance, are suitable for use in practice. This, however, restricts the ability to control the crosslinking temperature and/or the rate of the crosslinking reaction via the choice of the radical R, as is done with other blocked isocyanates.

There is therefore a need for crosslinking agents which have the advantages of the known tris(alkoxycarbonylamino)triazines but not their tendency to crystallize.

The invention accordingly provides the novel pyrimidine-based crosslinking agents for thermally curable compositions.

In the text below, the novel pyrimidine-based crosslinking agents are referred to as "crosslinking agents of the invention".

The invention also provides the novel thermally curable compositions which comprise the crosslinking agents of the invention and are referred to below as "compositions of the invention".

The invention provides not least the novel products which are produced from the compositions of the invention and are referred to below as "products of the invention".

The crosslinking agent of the invention comprises at least one derivative of pyrimidine.

Examples of suitable crosslinking agents of the invention are pyrimidines of the general formula I

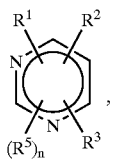

(I)

in which the variables and the index n have the following definition:

$n$=0 or 1

$R^1$ and $R^2$=identical or different radicals of the general formula II:

—NH—(CX)—YR$^4$  (II), in which the variables have the following definition:
X==O, =S;
Y==—O—, —S—, —NH—;
$R^4$=monovalent substituted or substituted $C_1$ to $C_{20}$ alkyl, $C_2$ to $C_{20}$ alkenyl, $C_4$ to $C_{12}$ cycloalkyl or cycloalkenyl, $C_6$ to $C_{12}$ aryl or $C_6$ to $C_{20}$ arylalkyl, arylalkenyl, arylcycloalkyl, arylcycloalkenyl, alkylaryl, alkenylaryl, cycloalkylaryl, cycloalkenylaryl, alkylcycloalkyl, alkylcycloalkenyl, alkenylcycloalkyl, alkenylcycloalkenyl, cycloalkylalkyl cycloalkenylalkyl, cycloalkylalkenyl or cycloalkenylalkenyl radical;
$R^5$=—F, —Cl, —Br, —I, —CN, —NO$_2$, substituted or unsubstituted, radical R4, substituted or unsubstituted radical —YR$^4$;
$R^3$=radical $R^1$ or $R^2$;
a radical of the general formulae III and IV:

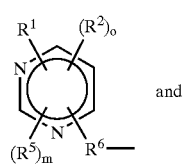

(III)

and

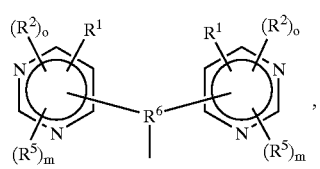

(IV)

in which the variables $R^1$, $R^2$, and $R^5$ have the definition stated. The indices m and o and the variable $R^6$ have the following definition:
$R^6$=alkane-, alkene-, cyclolkane- or cyclo-alkenediyl or -triyl radical or divalent or trivalent aromatic, aromatic-aliphatic, aromatic-cycloaliphatic, aromatic-olefinic or aromatic-cycloolefinic radical;
m=0, 1 or 2,
o=0 or 1;
with the proviso that if R3=a radical of the general formula IV, the radical R1 or R2 of the general formula I may also be a hydrogen atom.

The crosslinking agents of the invention are, in particular, mononuclear (general formula I), dinuclear (general formula I in conjunction with general formula III) and trinuclear (general formula I in conjunction with general formula IV) pyrimidines. It is also possible to employ higher polynuclear pyrimidines, although the technical effects achieved thereby do not always justify the increased synthesis effort.

In accordance with the invention, the mononuclear pyrimidines I are trifunctional in respect of thermal curing. This means that they have three radicals of the general formula II. Although, in specific cases, tetrafunctional mononuclear pyrimidines I are suitable, it is then often the case, for steric reasons, that all of the crosslinking groups (radicals of the general formula II) are no longer amenable to the crosslinking reaction, so that frequently the increased synthesis effort is unjustified.

In accordance with the invention, the dinuclear pyrimidines I/III are advantageously trifunctional or tetrafunctional in the sense referred to above, particularly trifunctional. Although, in specific cases, pyrimidines III of higher functionality may be suitable, such as pentafunctional or hexafunctional pyrimidines III, it is then often the case, for steric reasons, that all of the crosslinking groups (radials of the general formula II) are no longer amenable to the crosslinking reaction, so that the increased synthesis effort is in many cases unjustified.

In accordance with the invention, the trinuclear pyrimidines I/IV are advantageously tri-, tetra-, penta or hexafunctional in the sense referred to above, particularly tri- or tetrafunctional. Although, in very specific cases, pyrimidines I/IV of higher functionality may be suitable, such as hepta-, octa- or nonafunctional pyrimidines I/IV, it is then often the case, for steric reasons, that all of the crosslinking groups (radicals of the general formula II) are no longer amenable to the crosslinking reaction, so that the increased synthesis effort is in the great majority of cases unjustified.

In the general formula I, the radicals $R^1$ and $R^2$ stand for identical or different radicals of the general formula II. The decision as to whether identical or different radicals $R^1$ or $R^2$ are used is guided by whether it is desired to incorporate crosslinking centers, i.e., crosslinking functional groups, of differing reactivity. The skilled worker will therefore decide, on the basis of simple preliminary considerations, which possibility affords the most advantages in the case in hand.

In the general formula II, the variable X stands for an oxygen atom or a sulfur atom. In accordance with the invention, oxygen atoms are of advantage and are therefore used with preference.

The variable Y of the general formula II likewise stands for an oxygen atom or a sulfur atom and, in addition, for an amino group. In accordance with the invention, the oxygen atoms are of advantage here again and are therefore used with preference.

Accordingly, the radicals $R^1$ and $R^2$ used with preference in accordance with the invention comprise, very generally, carbamic esters which contain the above-described $R^4$s.

Examples of suitable, unsubstituted or substituted $C_1$–$C_{20}$ alkyl radicals $R^4$ for use in accordance with the invention are methyl, ethyl, propyl, butyl, pentyl, hexyl, heptyl, octyl, nonyl, decyl undecyl, dodecyl or pentadecyl radicals.

Examples of suitable substituted or unsubstituted $C_2$ to $C_{20}$ alkenyl, $C_4$ to $C_{12}$ cycloalkyl or cycloalkenyl, $C_6$ to $C_{12}$ aryl or $C_6$ to $C_{20}$ arylalkyl, arylalkenyl, arylcycloalkyl, arylcycloalkenyl, alkylaryl, alkenylaryl, cycloalkylaryl, cycloalkenylaryl, alkylcycloalkyl, alkylcycloalkenyl, alkenylcycloalkyl, alkenylcycloalkenyl, cycloalkylalkyl, cycloalkenylalkyl, cycloalkylalkenyl or cycloalkenylalkenyl radicals $R^4$ are

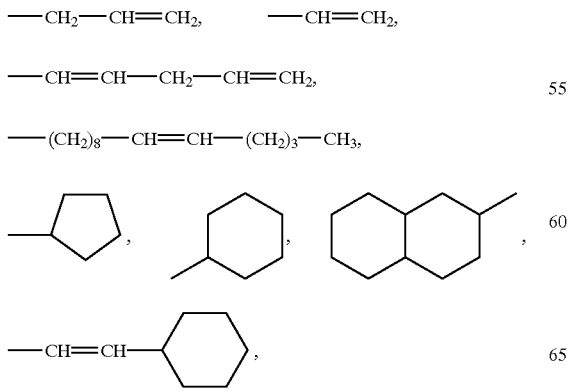

-continued

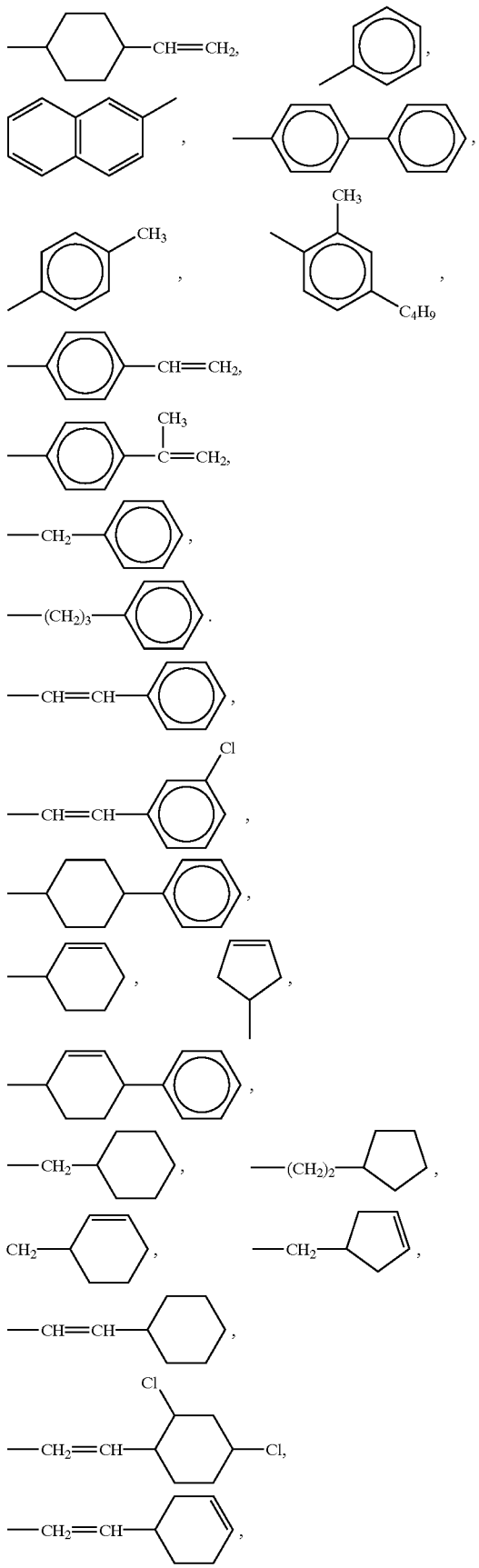

-continued

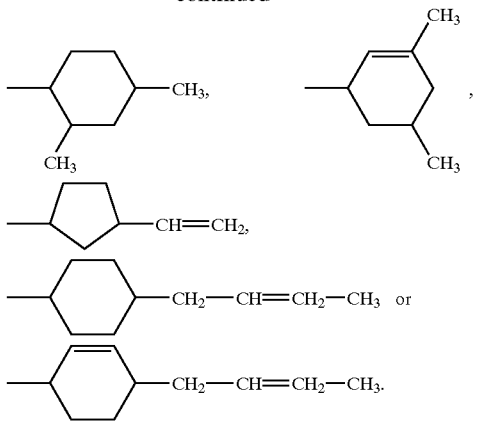

In accordance with the invention, methyl, ethyl, propyl, butyl radicals $R^4$ are of advantage since they are eliminated even at comparatively low temperatures, and the elimination products, especially the corresponding alcohols, are highly volatile, so that they can easily escape from the products of the invention.

The above-described radicals $R^4$ may have substituents. In very general terms, such substituents comprise groups such as are customary and known in the field of organic chemistry. It should be ensured, however that these groups do not interfere with, let alone suppress entirely, the crosslinking reactions of the crosslinking agents of the invention. Suitable substituents are therefore groups which are substantially inert with respect to the crosslinking reactions. The substituents afford the possibility, by way of steric and/or electronic effects, of varying the rate and/or the temperature of cleavage of the crosslinking centers of the crosslinking agents of the invention and hence the minimum crosslinking temperature and/or the rate of crosslinking in compositions of the invention. Examples of suitable substituents are fluorine, chlorine, bromine or iodine atoms, nitrile groups, nitro groups or alkyl ether or aryl ether groups.

The crosslinking agents of the invention may have the above-described substituents $R^5$. Examples of suitable substituted or unsubstituted radicals $R^4$, which may be used as radicals $R^5$ are those mentioned above. Examples of suitable substituted or unsubstituted radicals —$YR^4$ the ether groups or amino groups which have the above-described radicals $R^4$.

Accordingly, the index n of the general formula I is 0 or 1. Where the index n=0, this means in the context of the present invention that the crosslinking agent of the invention has a hydrogen atom in place of the radical $R^5$.

In accordance with the invention the reactivity of the crosslinking agents of the invention may be varied by means of the radicals $R^5$. However, this is necessary only in special cases.

The mononuclear pyrimidines I have a radical $R^3$ which has the definition of the radicals $R^1$ or $R^2$ described in detail above.

The dinuclear pyrimidines I/III, in contrast, contain a radical $R^3$ of the general formula III. In the general formula III the indices m and o have the definition indicated above. Accordingly, in the case of a trifunctional dinuclear pyrimidine I/III, the index o=0 and in the case of a tetrafunctional dinuclear pyrimidine I/III it=1.

In the dinuclear pyrimidines I/III, the two pyrimidine nuclei are linked with one another by way of the above-described divalent radical $R^6$. Examples of suitable divalent radicals $R^6$ are

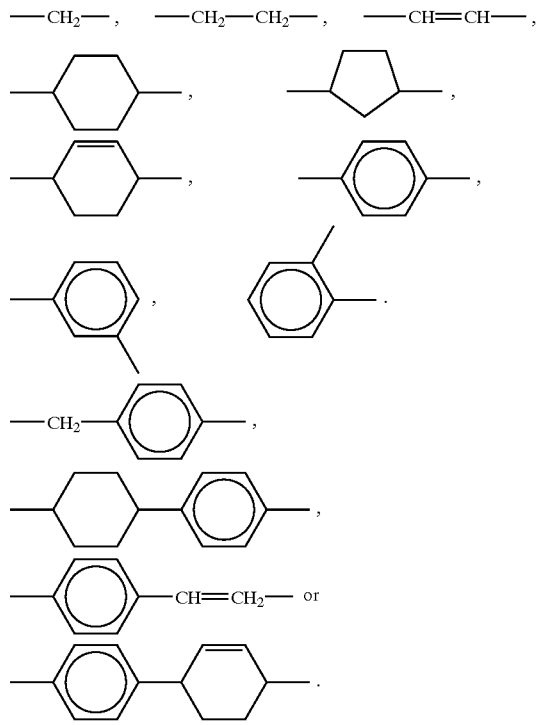

The trinuclear pyrimidines I/IV contain a radical $R^3$ of the general formula IV. In the general formula IV the indices m and o have the definition indicated above with the proviso indicated above. Accordingly, in the case of a trifunctional trinuclear pyrimidine I/IV of the index o is 0, and the radical $R^1$ or $R^2$ of the general formula I is a hydrogen atom.

In the trinuclear pyrimidines I/IV the three pyrimidine nuclei are linked with one another by way of the above-described trivalent radical $R^6$. Examples of suitable trivalent radicals $R^6$ are

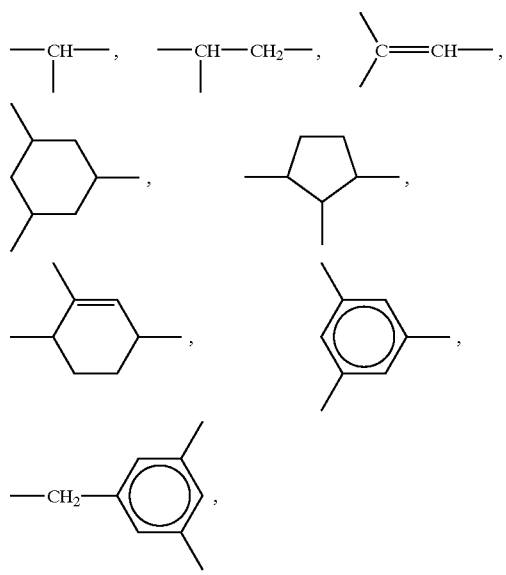

-continued

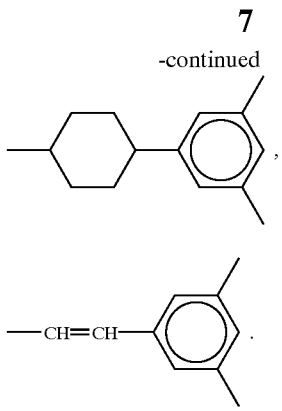

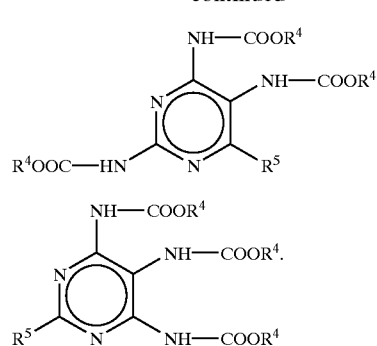 (I-5)

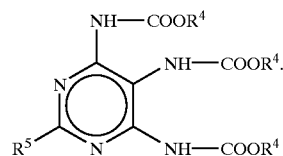 (I-6)

In accordance with the invention, the mononuclear pyrimidines I are of advantage, since owing to their smaller molecular size they lead to a denser network. Moreover, they are simpler to prepare then the di- or trinuclear pyrimidines I/III or I/IV. They are therefore used with particular preference in accordance with the invention.

In accordance with the invention, the mononuclear pyrimidines I of the general forms I in which the variables X and Y stand for oxygen atoms and the radical $R^4$ stands for $C_1$ to $C_{20}$ alkyl radicals, especially methyl, ethyl, propyl or butyl radicals, are of very particular advantage and are therefore used with very particular preference as crosslinking agents of the invention. Accordingly, the crosslinking agents of the invention which are very particularly preferred are tris(alkoxycarbonylamino)pyrimidines.

Examples of the very particularly preferred crosslinking agents of the invention are the tris(alkoxycarbonylamino) pyrimidines of the general formula (I-1) to (I-6), in which $R^4$ preferably stands for methyl, ethyl, propyl and/or butyl radicals.

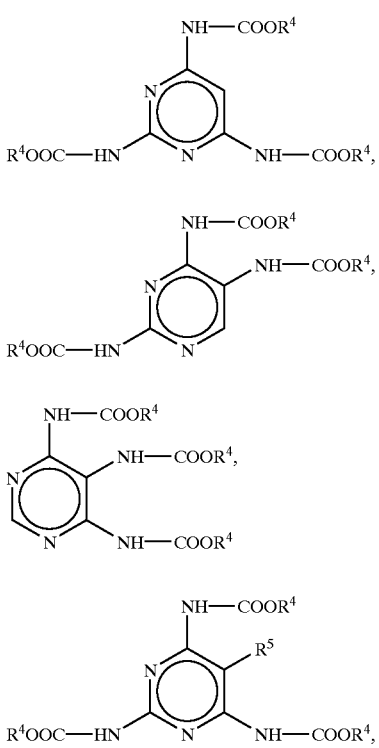

The very particularly preferred crosslinking agents of the invention accordingly comprise, or consist of, 2,4,6-, 2,4,5- and/or 2,3,4-tris(alkoxycarbonylamino)-pyrimidines I, especially 2,4,6-tris(alkoxycarbonylamino)pyrimidines I.

Very particularly outstanding technical effects are obtained through the use of the mixed derivative 2,4,6-tris (methoxy/butoxycarbonylamino)pyrimidine I.

The preparation of the crosslinking agents of the invention has no special features but instead takes place in accordance with the customary and known methods of organic chemistry. In particular, use is made of the preparation methods which have proven appropriate in the case of the tris(alkoxycarbonylamino)triazines.

For example, in analogy to the method described in the patent U.S. Pat. No. 4,939,213, polyisocyanatopyrimidines may be reacted with compounds containing a hydroxyl group or amino group, in particular a hydroxyl group, and also one of the radicals $R^4$ described in detail above to give the crosslinking agents of the invention. With very particular preference, methanol and/or butanol are used in this context.

Furthermore, in analogy to the method described in the patent EP-A-0 624 577, aminopyrimidines may be reacted with acyclic organic carbonates diethylcarbonate and/or dibutyl carbonate in the presence of alcoholates to give the crosslinking agents of the invention.

Not least, in analogy to the method described in patent U.S. Pat. No. 5,288,865, amino pyrimidines may be partly or fully halogenated with chlorine or bromine on their amino nitrogen atoms. The resulting N-halogen derivatives of the amino pyrimidines are then reacted with haloformic esters such as methyl chloroformate and/or butyl chloroformate to give the crosslinking agents of the invention.

The compositions of the invention comprise the crosslinking agents of the invention in an amount sufficient to give adequately cured products of the invention in the case of thermal curing. Depending on the case in hand, this amount is advantageously from 1 to 90% by weight, preferably from 2 to 80% by weight, with particular preference from 5 to 70% by weight, with very particular preference from 7 to 60% by weight, and in particular from 10 to 50% by weight, based on the respective composition of the invention.

As a further essential constituent the compositions of the invention comprise at least one constituent which reacts on heating with the crosslinking agents of the invention and in doing so builds up a three-dimensional network. This further essential constituent may be of low molecular mass, oligomeric or of high molecular mass. It is also possible to use mixtures of such constituents. Where the essential constituent comprises a low molecular mass constituent, it is generally referred to as a reactive diluent. Oligomeric or high molecular mass essential constituents of the type in question here are normally referred to by those in the art as binders.

The reactive diluents and/or binders used in accordance with the invention contain functional groups which react with the functional groups of the crosslinking agents of the invention, especially the alkoxycarbonyl amino groups. Examples of suitable functional groups of this kind are hydroxyl, thio and amino groups, especially hydroxyl groups.

Examples of suitable reactive diluents are linear, branched or hyperbranched polyols, especially aliphatic polyols such as tricyclodecanedimethanol, pentaerythritol, trimethylolpropane or $C_9$ to $C_{16}$ alkanes functionalized with at least two hydroxyl groups.

Examples of advantageous binders for use in accordance with the invention are hydroxyl-containing, linear and/or branched and/or block, comb and/or random, poly(meth)acrylates or acrylate copolymers, polyesters, alkyds, amino resins, polyurethanes, acrylated polyurethanes, acrylated polyesters, polylactones, polycarbonates, polyethers, epoxy resin-amine adducts, (meth)acrylate diols, partially saponified polyvinyl esters or polyureas, of which the acrylate copolymers, the polyesters, the polyurethanes, the polyethers and the epoxy resin-amine adducts are particularly advantageous and are therefore used with particular preference.

Furthermore, the compositions of the invention may comprise further customary and known crosslinking agents, such as, for example, the tris(alkoxycarbonyl-amino)triazines mentioned at the outset or crosslinking agents such as polyisocyanates, blocked polyisocyanates, melamine resins, benzoguanamine resins, urea-formaldehyde resins, siloxanes, polyanhydrides, beta-hydroxy-alkylamides, or compounds containing on average at least two groups capable of transesterification, examples being reaction products of malonic diesters and polyisocyanates or of esters and partial esters of polyhydric alcohols of malonic acid with monoisocyanates, as described the European patent EP-A-0 596 460.

Moreover, the compositions of the invention may comprise customary and known additives in effective amounts. The nature and amount of the additives are guided in particular by the intended use of the respective composition of the invention.

The compositions of the invention may not least also comprise constituents which are curable with actinic radiation. In the context of the present invention, actinic radiation means electron beams or, preferably, UV radiation. Curing by UV radiation is commonly initiated by free-radical or cationic photoinitiators. Where thermal curing and curing with actinic light are employed together, the term "dual cure" is also used.

The compositions of the invention may be present as solids, especially finely divided solids such as powders, as solvent-free, more or less viscous liquids, as powders dispersed in water, as aqueous or organic molecularly disperse solutions or as aqueous or organic dispersions or emulsions. The choice of forms is guided in particular by the intended use of the respective compositions of the invention.

The preparation of the compositions of the invention also has no special features but instead takes place with the aid of customary and known methods of the mixing of liquid and/or solid and also where appropriate, gaseous constituents in customary and known mixing units such as extruders, stirred tanks or dissolvers, for example.

The composition of the invention may be a thermally curable coating material, a thermally curable adhesive, a thermally curable sealing compound, or a thermally curable compound for producing moldings. These compositions of the invention cure thermally to give, as products of the invention, coatings or finishes, adhesive films, sealing compounds or moldings having outstanding performance properties. For these purposes, the compositions of the invention may be processed by the customary and known methods, which is a further advantage.

The crosslinking agents of the invention display their particular advantages above all in the coating materials of the invention.

The coating materials of the invention are used in particular to produce single-coat or multicoat, transparent, clear or matt, color and/or effect or electrically conductive or insulating coatings on any desired substrates, such as metals, plastics, wood, ceramic, stone, textile, fiber composites, leather, glass, glass fibers, glasswool and rock wool, mineral- and resin-bound building materials, such as plaster board and cement slabs or roof tiles, to which they may be applied by customary application methods, such as spraying, knife coating, brushing, flow coating, dipping trickling or rolling, for example.

The coating materials of the invention are outstandingly suitable in particular for automotive OEM finishing and automotive refinish, marine coating, industrial coating, including coil coating, container coating, wire enameling and electrical insulation coating, the coating of plastics, and furniture coating.

Preferred primed or unprimed substrates are therefore automobile body parts or industrial components, including containers or coils, made of metal and/or plastics, and also furniture of wood, glass, metal and/or plastics.

In this context the coating materials of the invention may be used to produce electrically conducting or electrically insulating coats, primers, electrocoats, primer-surfacer coats, basecoats, topcoats or clearcoats, but especially clearcoats and aqueous basecoats (waterborne basecoats and topcoats).

Where coating materials of the invention are used to produce topcoats or basecoats, they comprise customary and known color and/or effect pigments.

Otherwise, the coating materials of the invention may comprise, in addition to the reactive diluents and/or binders and the crosslinking agents of the invention, customary and known coatings additives, such as are described, for example, in the textbook "Lackadditive" [Additives for Coatings] by Johan Bieleman, Wiley-VCH, Weinheim, New York, 1998.

With very particular preference the coating materials of the invention are used to produce aqueous basecoats and/or clearcoats, in particular by the wet-on-wet technique. The wet-on-wet technique for the production of multicoat topcoat systems is described, for example, in the patents U.S. Pat. No. 3,639,147, DE-A-33 33 072, DE-A-38 14 853, GB-A-2 012 191, U.S. Pat. No. 3,953,644, EP-A-0 15 260 447, DE-A-39 03 804, EP-A-0 320 552, DE-A-36 28 124, U.S. Pat. No. 4,719,132, EP-A-0 297 576, EP-A-0 069 936, EP-A-0 089 497, EP-A-0 195 931, EP-A-0228 003, EP-A-0 038 127 and DE-A-28 18 100.

Examples of suitable aqueous basecoat materials for the wet-on-wet technique are known from the patents EP-A-0 089 497, EP-A-0 256 540, EP-A-0 260 447, EP-A-0 297 576, WO 96/12747, EP-A-0 523 610, EP-A-0 228 003, EP-A-0 397 806, EP-A-0 574 417, EP-A-0 531 510, EP-A-0 581 211, EP-A-0 708 788, EP-A-0 593 454, DE-A-43 28 092, EP-A-0 299 148, EP-A-0 394 737, EP-A-0 590 484, EP-A-0 234 362, EP-A-0 234 361, EP-A-0 543 817, WO 95/14721, EP-A-0 521 928, EP-A-0 522 420, EP-A-0 522 419, EP-A-0 649 865, EP-A-0 536 712, EP-A-0 596 460, EP-A-0 596 461, EP-A-0 584 818, EP-A-0 669 356, EP-A-0 634 431, EP-A-0 678 536, EP-A-0 354 261, EP-A-0 424 705, WO 97/49745, WO 97/49747, EP-A-0 401 565, EP—B-0 730 613 or WO 95/14721.

As is known, these aqueous basecoat materials are applied to primed or unprimed substrates, but are not baked, being instead subjected to initial drying. Then at least one clearcoat film is applied to the resulting, not fully cured coating film, after which the two coating films are baked together or baked and cured additionally with actinic radiation.

Suitable clearcoat materials in this context include one-component (1K), two-component (2K) or multicomponent (3K, 4K) clearcoat materials, powder clearcoat materials, powder slurry clearcoat materials, and clearcoat materials that are curable with actinic radiation.

Examples of suitable one-component (1K), two-component (2K) or multicomponent (3K, 4K) clearcoat materials are known, for example, from the patents DE-A-42 04 518, U.S. Pat. No. 5,474,811, U.S. Pat. No. 5,356,669, U.S. Pat. No. 5,605,965, WO 94/10211, WO 94/10212, WO 94/10213, EP-A-0 594 068, EP-A-0 594 071, EP-A-0 594 142, EP-A-0 604 992, WO 94/22969, EP-A-0 596 460 or WO 92/22615.

One-component(1K) clearcoat materials are known to comprise hydroxyl-containing binders and crosslinking agents such as blocked polyisocyanates, tris(alkoxycarbonylamino)triazines and/or amino resins. In another variant they comprise as binders polymers containing pendant carbamate and/or allophanate groups and carbamate- and/or allophanate-modified amino resins.

Two-component(2K) or multicomponent (3K, 4K) clearcoat materials are known to include as essential constituents hydroxyl-containing binders and polyisocyanate crosslinking agents, which are stored separately prior to their use.

Examples of suitable powder clearcoat materials are known, for example, from the German patent DE-A-42 22 194 or from the BASF Lacke+Farben AG product information "Pulverlacke" [Powder Coating Materials], 1990.

Powder clearcoat materials are known to include as essential constituents epoxy-functional binders and polycarboxylic acid crosslinking agents.

Examples of suitable powder slurry clearcoat materials are known, for example, from the US patent U.S. Pat. No. 4,268,542 and the German patent applications DE-A-195 18 392.4 and DE-A-196 13 547, or are described in the German patent application DE-A-198 14 471.7, unpublished at the priority date of the present specification.

Powder slurry clearcoat materials, as is known, comprise powder clearcoat materials dispersed in an aqueous medium.

UV-curable clearcoat materials are disclosed, for example, in the patents EP-A-0 540 884, EP-A-0 568 967 or U.S. Pat. No. 4,675,234.

Familiarly, they comprise low molecular mass, oligomeric and/or polymeric compounds which are curable with actinic light and/or electron beams, preferably radiation-curable binders, based in particular on ethylenically unsaturated prepolymers and/or ethylenically unsaturated oligomers; if desired, one or more reactive diluents; and also, if desired, one or more photoninitiators. Examples of suitable radiation-curable binders are (meth)acryloyl-functional, (meth)acrylic copolymers, polyether acrylates, polyester acrylates, unsaturated polyesters, epoxy acrylates, urethane acrylates, amino acrylates, melamine acrylates, silicone acrylates, and the corresponding methacrylates. Preference is given to using binders which are free from aromatic structural units.

It is, however, also possible to employ multicoat clearcoats, such as, for instance, a clearcoat based on hydroxyl-containing binders and blocked polyisocyanates and amino resin crosslinking agents, which lies directly atop the aqueous basecoat film and atop which there is a further clearcoat based, for example, on binders containing carbamate and/or allophanate groups and amino resin crosslinking agents.

In the case of the exemplified aqueous basecoat materials, one-component(1K) clearcoat materials, powder clearcoat materials and powder slurry clearcoat materials, in accordance with the present invention some or all of the customary and known crosslinking agents is replaced by the crosslinking agents of the invention.

In the case of the exemplified two-component(2K) or multicomponent(3K, 4K) clearcoat materials, the crosslinking agents of the invention are used as additional crosslinking agents alongside the polyisocyanates.

The UV-curable clearcoat materials, in contrast, may be used as dual-cure clearcoat materials for the additional use of the crosslinking agents of the invention.

These coating materials of the invention help to give coatings of the invention that are of high thermal, mechanical, and chemical stability. Noteworthy is their extremely high weathering stability, scratch resistance, hardness, and flexibility. Their overall appearance and their aesthetic effect is outstanding. This underlines the advantageous technical effect of the crosslinking agents of the invention.

Even complex primed or unprimed substrates, examples being automobile bodies, which comprise at least one coating of the invention, at least one adhesive film of the invention, at least one seal of the invention and/or at least one molding of the invention are superior to conventional substrates.

What is claimed is:

1. A pyrimidine-based crosslinking agent for thermally curable compositions, comprising one or more pyrimidines of the general formula I;

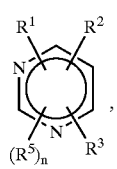

(I)

wherein:

n=0 or 1

$R^1$ and $R^2$=identical or different radicals of the general formula II:

—NH—(CX)—YR$^4$      (II), wherein X is selected from the group consisting of =O, and =S; Y is selected from the group consisting of —O—, —S—, and —NH—; and R is selected from the group consisting of monovalent substituted or substituted C1 to C20 alkyl, C2 to C20 alkenyl, C4 to C12 cycloalkyl or cycloalkenyl, C6 to C12 aryl or C6 to C20 arylalkyl, arylalkenyl, arylcycloalkyl, arylcycloalkehyl, alkylaryl, alkenylaryl, cycloalkylaryl, cycloalkenylaryl, alkylcycloalkyl, alkylcycloalkenyl, alkenylcycloalkyl, alkenylcycloalkenyl, cycloalkylalkyl, cycloalkenylalkyl, cycloalkylalkenyl and cycloalkenylalkenyl radicals;

$R^5$ is selected from the group consisting of —F, —Cl, —Br, —I, —CN, —NO$_2$, substituted or unsubstituted radical $R^4$, substituted or unsubstituted radical —YR$^4$; and $R^3$ is selected from the group consisting of radical $R^1$, radical $R^2$, a radical of the general formulae III and a radical of the general formulae IV;

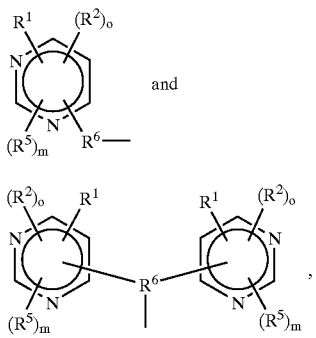

(III)

(IV)

in which the variables $R^1$, $R^2$, and $R^5$ are as defined above, and the indices m and o and the variable $R^6$ have the following definition:

$R^6$=alkane-, alkene-, cyclolkane- or cycloalkenediyl or -triyl radical or divalent or trivalent aromatic, aromatic-aliphatic, aromatic-cycloaliphatic, aromatic-olefinic or aromatic-cycloolefinic radical;

m=0, 1 or 2, o=0 or 1;

with the proviso that if $R^3$=a radical of the general formula IV, the radical $R^1$ or $R^2$ of the general formula I may also be a hydrogen atom.

2. The crosslinking agent of claim 1, comprising at least one of the tris(alkoxycarbonylamino)pyrimidines of the general formulae (I-1) to (I-6):

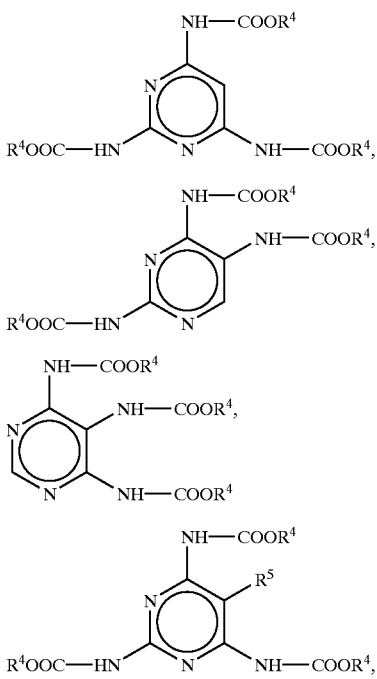

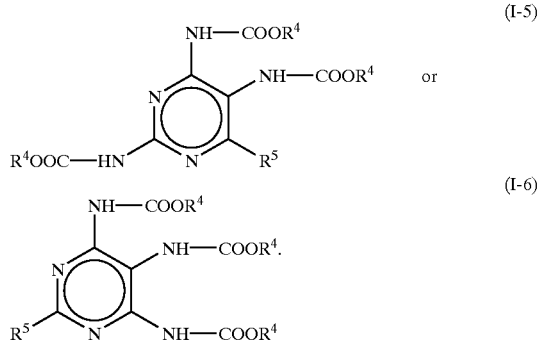

3. The crosslinking agent of claim 2, comprising 2,4,6-, 2,4,5 and/or 2,3,4-tris(alkoxycarbonylamino)pyrimidine.

4. The crosslinking agent of claim 3, comprising 2,4,6-tris(alkoxycarbonylamino)pyrimidine.

5. A process for preparing a thermally curable composition comprising mixing two or more constituents, wherein at least one constituent comprises the pyrimidine-based crosslinking agent of claim 1.

6. A thermally curable composition comprising at least one crosslinking agent as claimed in claim 1.

7. The thermally curable composition of claim 6 selected from the group consisting of a coating material, an adhesive, a sealing compound and a compound for producing moldings.

8. Single-coat or multicoat transparent, clear or matt, color and/or effect or electrically conductive coatings comprising a coating material as claimed in claim 7.

9. Single or multiple adhesive films comprising an adhesive as claimed in claim 7.

10. Seals comprising a sealing compound as claimed in claim 7.

11. Moldings comprising a compound for producing moldings as claimed in claim 7.

12. Primed or unprimed substrates comprising at least one coating as claimed in claim 8.

13. The primed or unprimed substrates of claim 12, further comprising one or more materials selected from the group consisting of metals, plastics, wood, ceramic, stone, textile, fiber composites, leather, glass, glass fibers, glass wool and rockwool, mineral- and resin-bound building materials, such as plasterboard and cement slabs or roof tiles, metals, plastics, wood, ceramic, stone, textile, fiber compositions, leather, glass, glass fibers, glass wool and rockwool, mineral- and resin-bound building materials, such as plasterboard and cement slabs or roof tiles, and composites of these materials.

14. The primed or unprimed substrates of claim 12, which are automobile body parts or industrial components.

15. The primed or unprimed substrates of claim 12 further comprising at least one molding as claimed in claim 11.

* * * * *